United States Patent [19]

Kempf et al.

[11] Patent Number: 5,455,351

[45] Date of Patent: Oct. 3, 1995

[54] RETROVIRAL PROTEASE INHIBITING PIPERAZINE COMPOUNDS

[75] Inventors: Dale J. Kempf, Libertyville; Daniel W. Norbeck, Crystal Lake; Hing L. Sham, Mundelein, all of Ill.

[73] Assignee: Abbott Laboratories, Abbott Park, Ill.

[21] Appl. No.: 166,369

[22] Filed: Dec. 13, 1993

[51] Int. Cl.$^6$ .................... C07D 413/06; C07D 413/14; C07D 417/06; C07D 417/14

[52] U.S. Cl. .................... 544/366; 544/60; 544/121; 544/133; 544/137; 544/238; 544/333; 544/364; 544/369

[58] Field of Search .................... 514/231.5, 235.8, 514/255; 544/121, 364, 369, 60, 133, 137, 238, 333, 366

[56] References Cited

FOREIGN PATENT DOCUMENTS

| 541168 | 5/1993 | European Pat. Off. |
| WO92/08701 | 5/1992 | WIPO |
| WO93/09132 | 5/1993 | WIPO |

Primary Examiner—Yogendra N. Gupta

Attorney, Agent, or Firm—Steven R. Crowley

[57] ABSTRACT

Retroviral protease inhibiting compounds of the formula:

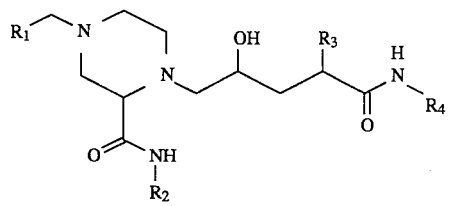

and

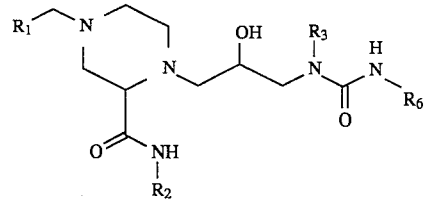

are disclosed.

7 Claims, No Drawings

RETROVIRAL PROTEASE INHIBITING PIPERAZINE COMPOUNDS

TECHNICAL FIELD

The present invention relates to novel compounds and a composition and method for inhibiting retroviral proteases and in particular for inhibiting human immunodeficiency virus (HIV) protease, a composition and method for treating a retroviral infection and in particular an HIV infection, processes for making such compounds and synthetic intermediates employed in these processes.

BACKGROUND OF THE INVENTION

Retroviruses are those viruses which utilize a ribonucleic acid (RNA) intermediate and a RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV- 1 and HIV-2), which cause acquired immune deficiency syndrome (AIDS) in man, hepatitis B virus, which causes hepatitis and hepatic carcinomas in man, human T-cell lymphotrophic viruses I, II, IV and V, which cause human acute cell leukemia, and bovine and feline leukemia viruses which cause leukemia in domestic animals.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. An inhibitor of a retroviral protease will provide a therapeutic agent for diseases caused by the retrovirus.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into core proteins, and also process the pol precursor into reverse transciptase and retroviral protease. In addition, retroviral proteases are sequence specific. See Pearl, Nature 328 482 (1987).

The correct processing of the precursor polyproteins by the retroviral protease is necessary for the assembly of infectious virions. It has been shown that in vitro mutagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

Current treatments for viral diseases usually involve administration of compounds that inhibit viral DNA synthesis. Current treatments for AIDS involve administration of compounds such as 3'-azido- 3'-deoxythymidine (AZT), 2',3'-dideoxycytidine (DDC) and 2',3'-dideoxyinosine (DDI) and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

DISCLOSURE OF THE INVENTION

In accordance with the present invention, there are retroviral protease inhibiting compounds of the formula A1:

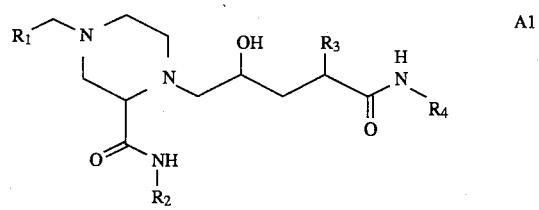

wherein $R_1$ is thiazolyl, oxazolyl, monosubstituted thiazolyl or monosubstituted oxazolyl wherein the substituent is selected from (i) loweralkyl, (ii) loweralkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy, (viii) (heterocyclic)alkyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, loweralkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

$R_2$ is loweralkyl;

$R_3$ is benzyl or benzyl in which the phenyl group is substituted with loweralkyl, —OH, halo, alkoxy, trifluoromethyl, 2-(4-morpholinyl)ethoxy or 2-hydroxyethoxy; and $R_4$ is

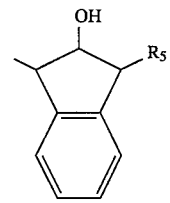

wherein $R_5$ is hydrogen, —OH or —NH$_2$; or a pharmaceutically acceptable salt, ester or prodrug thereof.

Preferred compounds of the formula A1 are those wherein $R_1$ is thiazolyl, oxazolyl, monosubstitued thiazolyl or monosubstituted oxazolyl wherein the substituent is selected from loweralkyl, cycloalkyl or cycloalkylalkyl; $R_2$ is t-butyl, isopropyl or t-butylmethyl; $R_3$ is benzyl and $R_5$ is hydrogen.

More preferred compounds of the formula A1 are those of the formula A2:

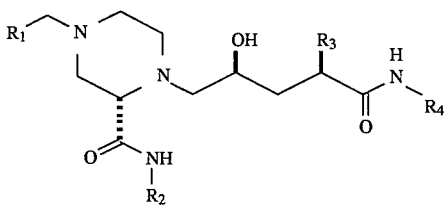

wherein $R_1$ is thiazolyl, oxazolyl, monosubstituted thiazolyl or monosubstituted oxazolyl wherein the substituent is selected from (i) loweralkyl, (ii) loweralkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy, (viii) (heterocyclic)aikyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, loweralkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

$R_2$ is loweralkyl;

$R_3$ is benzyl or benzyl in which the phenyl group is substituted with loweralkyl, —OH, halo, alkoxy, trifluoromethyl, 2-(4-morpholinyl)ethoxy or 2-hydroxyethoxy; and $R_4$ is

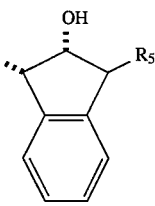

wherein $R_5$ is hydrogen, —OH or —NH$_2$; or a pharmaceutically acceptable salt, ester or prodrug thereof.

Preferred compounds of the formula A2 are those wherein $R_1$ is thiazolyl, oxazolyl, monosubstitued thiazolyl or monosubstituted oxazolyl wherein the substituent is selected from loweralkyl, cycloalkyl or cycloalkylalkyl; $R_2$ is t-butyl, isopropyl or t-butylmethyl; $R_3$ is benzyl and $R_4$ is

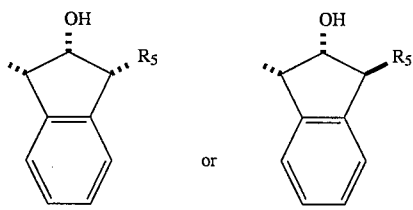

wherein $R_5$ is hydrogen, —OH or —NH$_2$.

More preferred compounds of the formula A2 are those wherein $R_1$ is thiazolyl, oxazolyl, monosubstitued thiazolyl or monosubstituted oxazolyl wherein the substituent is selected from loweralkyl, cycloalkyl or cycloalkylalkyl; $R_2$ is t-butyl, isopropyl or t-butylmethyl; $R_3$ is benzyl and $R_5$ is hydrogen.

In accordance with the present invention, there are also retroviral protease inhibiting compounds of the formula A3:

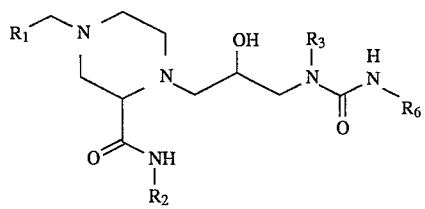

wherein $R_1$ is thiazolyl, oxazolyl, monosubstituted thiazolyl or monosubstituted oxazolyl wherein the substituent is selected from (i) loweralkyl, (ii) loweralkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy, (viii) (heterocyclic)alkyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, loweralkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

$R_2$ is loweralkyl;

$R_3$ is loweralkyl, benzyl or benzyl in which the phenyl group is substituted with loweralkyl, —OH, halo, alkoxy, trifluoromethyl, 2-(4-morpholinyl)ethoxy or 2-hydroxyethoxy; and $R_6$ is loweralkyl or

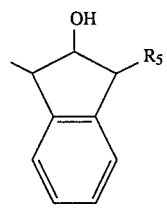

wherein $R_5$ is hydrogen, —OH or —NH$_2$; or a pharmaceutically acceptable salt, ester or prodrug thereof.

Preferred compounds of the formula A3 are those wherein $R_1$ is thiazolyl, oxazolyl, monosubstitued thiazolyl or monosubstituted oxazolyl wherein the substituent is selected from loweralkyl, cycloalkyl or cycloalkylalkyl; $R_2$ is t-butyl, isopropyl or t-butylmethyl; $R_3$ is loweralkyl or benzyl and $R_6$ is loweralkyl or

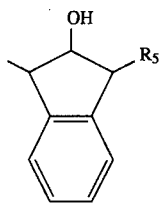

wherein R₅ is hydrogen.

More preferred compounds of the formula A3 are those of the formula A4:

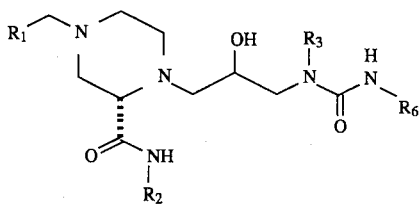

wherein R₁ is thiazolyl, oxazolyl, monosubstituted thiazolyl or monosubstituted oxazolyl wherein the substituent is selected from (i) loweralkyl, (ii) loweralkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy, (viii) (heterocyclic)alkyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, loweralkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

R₂ is loweralkyl;

R₃ is loweralkyl, benzyl or benzyl in which the phenyl group is substituted with loweralkyl, —OH, halo, alkoxy, trifluoromethyl, 2-(4-morpholinyl)ethoxy or 2-hydroxyethoxy; and R₆ is loweralkyl or

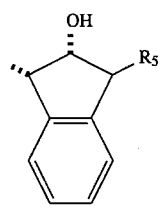

wherein R₅ is hydrogen, —OH or —NH₂; or a pharmaceutically acceptable salt, ester or prodrug thereof.

Preferred compounds of the formula A4 are those wherein R₁ is thiazolyl, oxazolyl, monosubstitued thiazolyl or monosubstituted oxazolyl wherein the substituent is selected from loweralkyl, cycloalkyl or cycloalkylalkyl; R₂ is t-butyl, isopropyl or t-butylmethyl; R₃ is loweralkyl or benzyl and R₆ is loweralkyl or

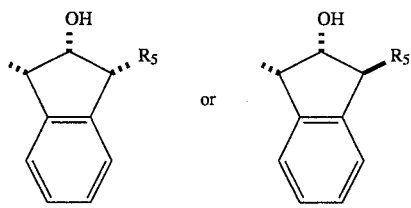

wherein R₅ is hydrogen, —OH or —NH₂.

More preferred compounds of the formula A4 are those wherein R₁ is thiazolyl, oxazolyl, monosubstitued thiazolyl or monosubstituted oxazolyl wherein the substituent is selected from loweralkyl, cycloalkyl or cycloalkylalkyl; R₂ is t-butyl, isopropyl or t-butylmethyl; R₃ is loweralkyl or benzyl and R₆ is loweralkyl or

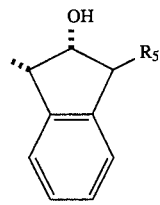

wherein R₅ is hydrogen.

The compounds of the invention comprise asymmetrically substituted centers (i.e., asymmetrically substituted carbon atoms). The present invention is intended to include all stereoisomeric forms of the compounds, including racemic mixtures, mixtures of diastereomers, as well as single diastereomers of the compounds of the invention. The terms "S" and "R" configuration are as defined by the IUPAC 1974 Recommendations for Section E, Fundamental Stereochemistry, Pure Appl. Chem. (1976) 45, 13– 30.

The terms "Val" and "Ala" as used herein refer to valine and alanine, respectively. Unless otherwise noted, when "Val" and "Ala" are used herein they refer to the L-isomer. In general, the amino acid abbreviations used herein follow the IUPAC-IUB Joint Commission on Biochemical Nomenclature for amino acids and peptides (Eur. J. Biochem. 1984, 158, 9–31).

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5- dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "O-protecting group" as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981 )). O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "loweralkenyl" as used herein refers to a straight or branched chain alkyl radical containing from 2 to 6 carbon atoms and also having one carbon-carbon double bond including, but not limited to, vinyl, 2-propenyl, 2-methyl-2-propenyl, 3-butenyl, 4-pentenyl, 5-hexenyl and the like.

The term "phenyl" as used herein refers to a phenyl group which is unsubstituted or substituted with a substituent selected from loweralkyl, alkoxy, thioalkoxy, hydroxy and halo.

The term "phenylalkyl" as used herein refers to an phenyl group appended to a loweralkyl radical including, but not limited to, benzyl, 4-hydroxybenzyl, 4-chlorobenzyl, 1-naphthylmethyl and the like.

The term "alkylamino" as used herein refers to a loweralkyl radical appended to an —NH radical.

The term "cycloalkyl" as used herein refers to an aliphatic ring having 3 to 7 carbon atoms including, but not limited to, cyclopropyl, cyclopentyl, cyclohexyl and the like. A preferred cycloalkyl group is cyclopropyl.

The term "cycloalkylalkyl" as used herein refers to a cycloalkyl group appended to a loweralkyl radical, including but not limited to cyclohexylmethyl.

The term "cycloalkenyl" as used herein refers to to an aliphatic ring having 5 to 7 carbon atoms and also having one carbon-carbon double bond including, but not limited to, cyclopentenyl, cyclohexenyl and the like.

The term "cycloalkenylalkyl" as used herein refers to a cycloalkenyl group appended to a loweralkyl radical including, but not limited to, cyclopentenylmethyl, cyclohexenylmethyl and the like.

The terms "alkoxy" and "thioalkoxy" as used herein refer to $R_{15}O—$ and $R_{15}S—$, respectively, wherein $R_{15}$ is a loweralkyl group or benzyl.

The term "alkoxyalkyl" as used herein refers to an alkoxy group appended to a loweralkyl radical.

The term "thioalkoxyalkyl" as used herein refers to a thioalkoxy group appended to a loweralkyl radical.

The term "dialkylamino" as used herein refers to —$NR_{16}R_{17}$ wherein $R_{16}$ and $R_{17}$ are independently selected from loweralkyl groups.

The term "dialkylaminoalkyl" as used herein refers to —$NR_{18}R_{19}$ which is appended to a loweralkyl radical wherein $R_{18}$ and $R_{19}$ are independently selected from loweralkyl.

The term "halo" or "halogen" as used herein refers to —Cl, —Br, —I or —F.

The term "heterocyclic" as used herein refers to a heterocyclic group selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy.

The term "(heterocyclic)alkyl" as used herein refers to a heterocyclic group appended to a loweralkyl radical including, but not limited to, pyrrolidinylmethyl and morpholinylmethyl.

The term "activated ester derivative" as used herein refer to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

In the compounds of the invention, combinations of substituents and/or variables are permissible only if such combinations result in stable compounds. As used herein, the term "stable compound" refers to a compound that is sufficiently stable to survive isolation to a useful degree of purity from a reaction mixture and formulation into a therapeutic dosage form suitable for administration.

The compounds of the invention can be prepared as shown in Schemes 1–2.

According to Scheme I, sequential N-protection of aminoacid I (for example, by reaction of aminoacid I with N-carbobenzyloxysuccinimide and then with Boc-ON) yields the bis-carbamate II. Coupling of the carboxylic acid group in II (or an activated ester derivative thereof) to $R_2NH_2$ leads to amide III. Deprotection of the t-butylcarbamate moiety in III provides the intermediate piperazine IV. The hydroxylactone V is O-protected (for example, as its t-butyldimethylsilyl ether) to give VI. Alkylation of the enolate derived from VI (generated with a non-nucleophilic strong base such as lithium diisopropylamide) with $R_3$-X (wherein X is a leaving group such as a halide, a mesylate or a tosylate and the like) stereoselectively provides the lactone VII, which is deprotected to give hydroxylactone VIII. The hydroxy group of VIII is converted to a leaving group (for example, a trifluoromethanesulfonyl group and the like) to give IX. Reaction of IX with piperazine IV provides intermediate X. Hydrolysis of X, followed by protection of the resulting free hydroxyl group (for example, as the t-butyldimethylsilylether and the like) provides carboxylic acid XI. Carboxylic acid XI or an activated ester derivative thereof is coupled to $R_4NH_2$ to provide XII, which is deprotected at the hydroxyl group to give XIII. The Cbz group of XIII is removed by hydrogenolysis to provide penultimate intermediate XIV. Alkylation of XIV with $R_1CH_2X'$ (wherein X is a leaving group such as a halide, a mesylate or a tosylate and the like) provides compound XV.

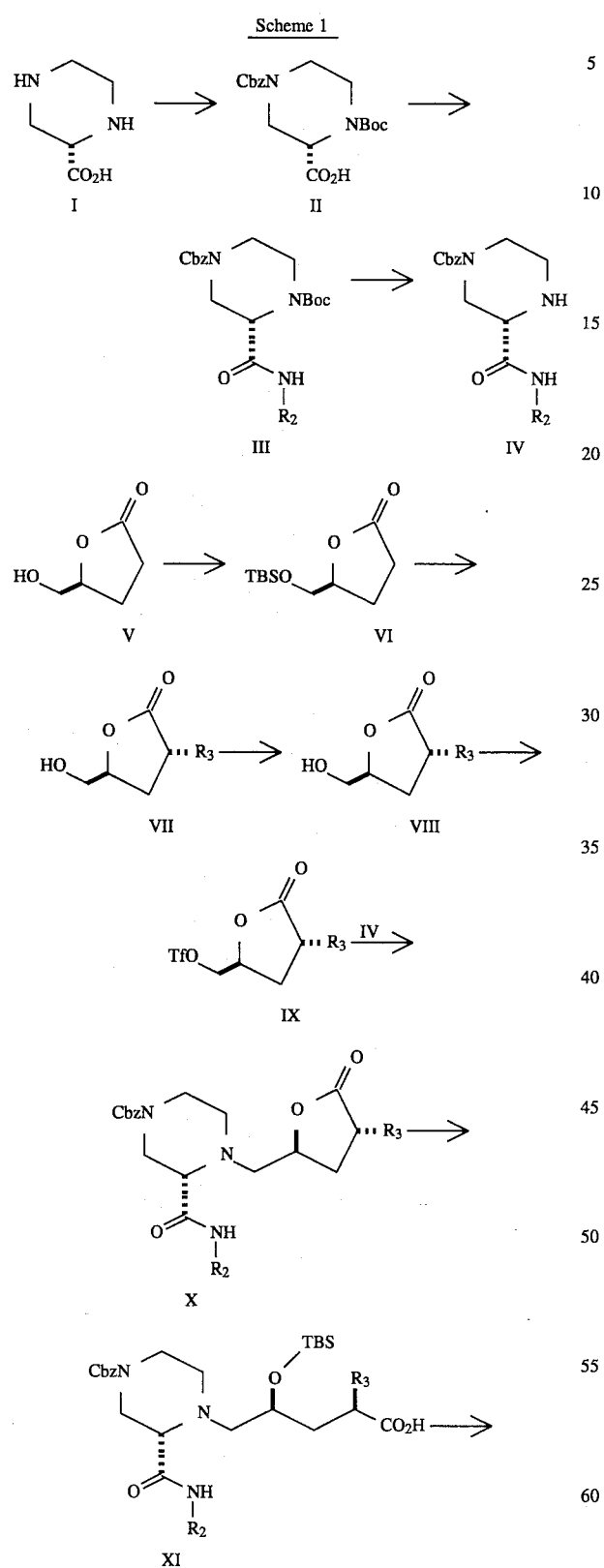

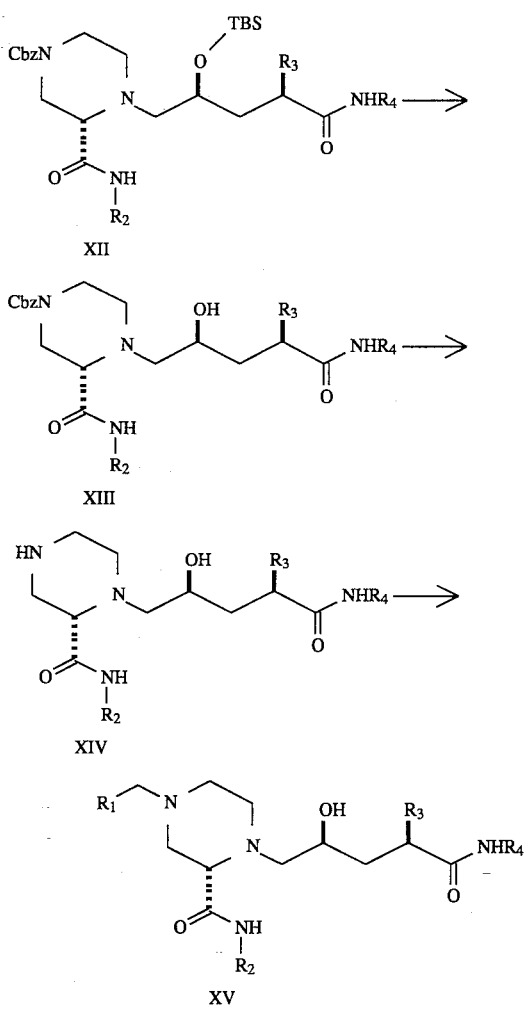

According to Scheme II, allylation of carbamate XVI (NaH, allyl bromide) provides XVII, which upon epoxidation (MCPBA) gives XVIII. Alkylation of piperazine IV with XVIII provides XIX. Deprotection of XIX (HCl or TFA) gives XX, which, upon treatment with an isocyanate $R_6NCO$, provides XXI. Hydrogenolytic removal of the Cbz group of XXI gives XXII, which, upon alkylation with $R_1CH_2X'$ (wherein X' is a leaving group such as a halide, a mesylate or a tosylate and the like) provides compound XXIII.

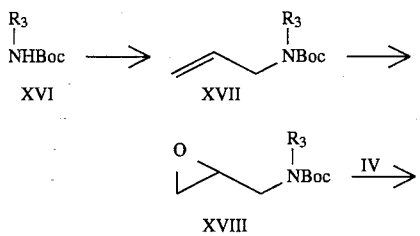

-continued
Scheme 2

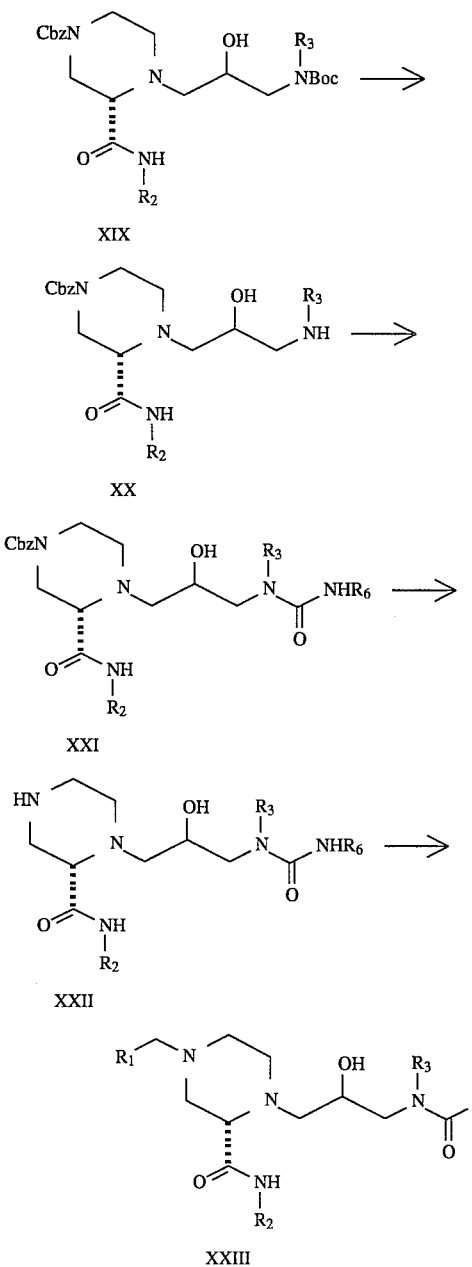

The following examples will serve to further illustrate the preparation of the novel compounds of the invention.

EXAMPLE 1

A.
2(S)-4-(Benzyloxycarbonyl)-1-(t-butyloxycarbonyl)piperazine-2-carboxylic Acid 2(S)-Piperazine-2-carboxylic acid (Felder, et al., Helv. Chim. Acta, 1960, 43, 888) (10.0 g, 49.5 mmol) was dissolved in 100 ml of 1:1 dioxane:$H_2O$. The pH of the solution was adjusted to 11 with 1 N NaOH. To the resulting solution was added dropwise over 1 h a solution of 13.57 g (54.5 mmol) of N-((benzyloxycarbonyl)oxy)succinimide in 50 ml of dioxane. Periodically during the addition, the pH was readjusted to 11 with 1 N NaOH. After addition, the solution was stirred at ambient temperature for 2.5 h, after which tlc analysis revealed the absence of starting material. The pH of the solution was adjusted to 9.5, and the solution was treated dropwise with a solution of 13.42 g (54.5 mmol) of [2-(tert-butoxycarbonyloxyimino)- 2-phenylacetonitrile. During addition, the pH was periodically adjusted to 9.5 with 1 N NaOH. After addition, the resulting solution was stirred at ambient temperature for 16 h, basified with NaOH, washed with three portions of ether, acidified with 6 N HCl, and extracted with five 150 ml portions of ethyl acetate. The combined organic layers were dried over $Na_2SO_4$ and concentrated in vacuo. Trituration of the residue with $CH_2Cl_2$, hexane followed by removal of the solvent in vacuo provided the crude desired compound (13.85 g, 77%), which was used without further purification, as an off-white foam. Mass spectrum: $(M+NH_4)^+=182$.

B. N-(t-Butyl)-4-(benzyloxycarbonyl)-1-(t-butyloxycarbonyl)piperazine- 2-carboxamide A solution of 13.85 g (38.0 mmol) of 2(S)-4-(benzyloxycarbonyl)- 1-(t-butyloxycarbonyl)piperazine-2-carboxylic acid and 9.94 ml (57 mmol) of diisopropylethylamine in 200 ml of dimethylformamide was treated sequentially with 7.7 g (57 mmol) of 1-hydroxybenzotriazole and 10.93 g (57 mmol) of ethyl (dimethylaminopropyl)carbodiimide hydrochloride. The resulting mixture was treated with 6.0 ml (57 mmol) of t-butylamine and stirred at ambient temperature for 16 h. After removal of the solvent in vacuo, the crude residue was partitioned between 800 ml of ethyl acetate and 100 ml of water. The organic layer was washed with 1 N HCl, saturated aqueous $NaHCO_3$, water, and saturated brine. After being dried over $MgSO_4$, the organic phase was concentrated in vacuo to yield a foam. Silica gel chromatography of the residue using first 20% then 30% ethyl acetate in chloroform provided 10.43 g (65%) of the desired compound as a foam. $^1H$ NMR $(CDCl_3)$ δ1.31 (s, 9H), 1.48 (s, 9H), 3.15 (m, 3H), 3.9 (m, 2H), 4.5 (m, 2H), 5.15 (m, 2H), 5.85 (br, 1H), 7.35 (m, 5H). Mass spectrum: $(M+H)^+=420$.

C. N-(t-Butyl)-4-(benzyloxycarbonyl)piperazine-2-carboxamide

A solution of 14.2 g (33.9 mmol) of N-(t-butyl)-4-(benzyloxycarbonyl)- 1-(t-butyloxycarbonyl)piperazine-2-carboxamide in 100 ml of dichloromethane was treated with 20 ml of trifluoroacetic acid. The resulting solution was stirred at ambient temperature for 3 h, concentrated in vacuo, and treated with 800 ml of ethyl acetate. The solution was washed with 1 N NaOH. The aqueous layer was extracted with two portions of ethyl acetate, and the combined organic layers were washed with saturated brine, dried over $MgSO_4$, and concentrated in vacuo. Silica gel chromatography of the residue using first 2% then 4% methanol in chloroform provided 8.42 g (78%) of the desired compound. $^1H$ NMR $(CDCl_3)$δ1.34 (s, 9H), 2.8 (m, 1H), 3.0 (m, 3H), 3.21 (dd, J=9, 4 Hz, 1H), 3.9 (m, 1H), 4.2 (m, 1H), 5.14 (AA', 2H), 6.6 (br, 1H), 7.3–7.4 (m, 5H). Mass spectrum: $(M+H)^+=320$.

D. (5S)-5-((t-Butyldimethylsilyloxy)methyl) dihydrofuran-2(3H)-one

A solution of 13.2 g (113 mmol) of (5S)-dihydro-5-(hydroxymethyl)furan- 2(3H)-one in 200 ml of dimethylformamide was treated sequentially with 9.28 g (136 mmol) of imidazole and 18.84 g (125 mmol) of chloro-t-butyldim-

E. (2R,5S)-2-Benzyl-5-((t-butyldimethylsilyloxy) methyl)dihydrofuran-2(3H)-one ethylsilane, the latter in several portions. The resulting solution was stirred at ambient temperature for 6 h, poured into 10% aqueous citric acid, and extracted with ethyl acetate. The organic layer was washed sequentially with two portions of water, one portion of aqueous NaHCO$_3$ and one portion of saturated brine. The organic layer was dried over MgSO$_4$, and concentrated in vacuo to provide 22.04 g (90%) of the desired compound.

E. (2R,5S)-2-Benzyl-5-((t-butyldimethylsilyloxy) methyl)dihydrofuran-2(3H)-one A solution of 12.44 of (5S)-5-((t-butyldimethylsilyloxy)methyl)-dihydrofuran- 2(3H)-one in 250 ml of anhydrous tetrahydrofuran was cooled to −78° C. and treated via cannula over a 30 min period with 100 ml (62.2 mmol) of lithium diisopropylamide in heptane/tetrahydrofuran/ethylbenzene. The resulting solution was stirred for 30 min at −78° C., treated dropwise with 7.39 ml (62 mmol) of benzyl bromide, and stirred at −78° C. for an additional 3 h. After addition of aqueous citric acid, the solution was allowed to warm and extracted with three 250 ml portions of ethyl acetate. The combined organic layers were washed with water, aqueous NaHCO$_3$ and saturated brine, dried over MgSO$_4$, and concentrated in vacuo. Silica gel chromatography of the residue using first 10% then 20% ethyl acetate in hexane provided 11.13 g (64%) of the desired compound. $^1$H NMR (CDCl$_3$) δ0.04 (s, 3H), 0.05 (s, 3H), 0.87 (s, 9H), 2.01 (m, 1H), 2.19 (m, 1H), 2.72 (dd, J=13, 9 Hz, 1H), 3.09 (tq, J=10, 4 Hz, 1H), 3.23 (dd, J=13, 5 Hz, 1 H), 3.61 (m, 1H), 3.81 (dd, J=12, 3 Hz, 1H), 4.40 (dq, J=8, 3 Hz, 1H), 7.2– 7.35 (m, 5H). Mass spectrum: (M+NH$_4$)$^+$=338.

F. (3R,5S)-3-Benzyl-5-(hydroxymethyl) dihydrofuran-2(3H)-one

A solution of 11.13 g (34.8 mmol) of (2R,5S)-2-benzyl-5 -((t-butyldimethylsilyloxy)methyl)dihydrofuran- 2(3H)-one in 100 ml of acetonitrile was treated with 2.83 ml of 50% aqueous HF, stirred at ambient temperature for 3 h, and concentrated in vacuo to an oil. The oil was partitioned between ethyl acetate and water. The organic phase was dried over MgSO$_4$ and concentrated in vacuo. Silica gel chromatography of the residue using first 20% then 40% ethyl acetate in chloroform provided 4.86 g (68%) of the desired compound. $^1$H NMR (CDCl$_3$) δ2.05 (m, 1H), 2.18 (ddd, J=13, 10, 5 Hz, 1H), 2.80 (dd, J=13, 9 Hz, 1H), 3.05 (m 1H), 3.20 (dd, 15, 5 Hz, 1H), 3.59 (dd, J=13, 5 Hz, 1H), 3.81 (dd, J =12, 3 Hz, 1H), 4.39 (m, 1H), 7.2–7.4 (m, 5H). Mass spectrum: (M+NH$_4$)$^+$=224.

G. (3R,5S)-3-Benzyl-5-(((trifluoromethyl)sulfonyl) oxymethyl)dihydrofuran- 2(3H)-one A solution of 4.47 g (21.6 mmol) of (3R,5S)-3-benzyl-5- (hydroxymethyl)dihydrofuran- 2(3H)-one and 3.27 ml (28.1 mmol) of 2,6-lutidine in 100 ml of dichloromethane was cooled in an ice-salt bath (−5° C.) and treated dropwise over 30 min with 3.99 ml (23.8 mmol) of trifluoromethanesulfonic anhydride. The resulting solution was stirred at −5° C. for 1 h, poured over ice/brine, and extracted in three 200 ml portions of chloroform. The combined organic layers were washed with 1 N HCl, aqueous NaHCO$_3$ and saturated brine, dried over MgSO$_4$, and concentrated in vacuo. Silica gel chromatography of the residue using first 10% then 25% ethyl acetate in hexane provided 4.61 g (63%) of the desired compound as a white solid.

H. (3R,5S2'S)-3-Benzyl-5-((((4-(benzyloxycarbonyl)-2- (t-butyl)amino)carbonyl)piperazin- 1-yl)methyl)dihydrofuran-2(3H)-one A solution of 4.61 g (13.64 mmol) of N-(t-butyl)-4- (benzyloxycarbonyl)piperazine- 2-carboxamide and 1.91 ml (16.4 mmol) of 2,6-lutidine in 200 ml of isopropyl alcohol was treated with 4.61 g (13.64 mmol) of (3R,5S)-3-benzyl-5-(((trifluoromethyl)sulfonyl)oxymethyl)dihydrofuran-2(3H)-one and stirred at ambient temperature. After 1 h, an additional portion (0.5 g) of (3R,5S)-3-benzyl- 5-(((trifluoromethyl)sulfonyl)oxymethyl)dihydrofuran-2(3H)-one was added, and stirring was continued for 1 h. The solvent was removed in vacuo, and the residue was purified by silica gel chromatography using a gradient of 15%–50% ethyl acetate in chloroform to provide 3.47 g (50%) of the desired compound as an oil. $^1$H NMR (CDCl$_3$)δ1.35 (s, 9H), 1.84 (m, 1H), 2.05–2.2 (m, 2H), 2.25 (br d, J=13 Hz, 1H), 2.6–2.75 (m, 2H), 2.8– 3.0 (m, 5H), 3.16 (dd, J=13, 3 Hz, 1H), 4.02 (m, 1H), 4.22 (br d, J=13 Hz, 1H), 4.40 (br q, J=9 Hz, 1H), 5.12 (AA', 2H), 6.65 (br, 1H), 7.15–7.35 (m, 10H). Mass spectrum: (M+H)$^+$=508.

I. (2R,4S,2'S)-5-(((4-(Benzyloxycarbonyl)-2-(t-butyl) amino)carbonyl)piperazin- 1-yl)-4-((t-butyldimethyisilyl)oxy)-1-phenyl- 2-carboxylic Acid A solution of 3.47 g (6.84 mmol) of (3R,5S2'S)-3-benzyl-5((((4-(benzyloxycarbonyl)- 2-(t-butyl)amino)carbonyl)piperazin-1-yl)methyl)- 3,4-tetrahydro[5H]furan-2-one in 16 ml of dimethoxyethane was cooled to 0° C. and treated sequentially with 8 ml of water and 196 mg (8.2 mmol) of lithium hydroxide. After being stirred for 45 min, the resulting solution was acidified to pH 6 with 1 N HCl and concentrated in vacuo. The remainder was partitioned between 15 ml of water and five 50 ml portions of ethyl acetate. The combined organic layers were washed with saturated brine, dried over MgSO$_4$, and concentrated in vacuo to provide the crude desired compound, which was used without further purification.

J. (1S,2R,2'R,4'S,2"S)-1-((2-Benzyl-5- (((4-(benzyloxycarbonyl)- 2-(t-butyl)amino)carbonyl)piperazin-1-yl)-4- ((t-butyldimethylsilyl)oxy)pentanoyl)amino)indan-2-ol A solution of 225 mg (0.34 mmol) of (2R,4S,2'S)-5-(((4- (benzyloxycarbonyl)- 2-(t-butyl)amino)carbonyl)piperazin-1-yl)-4-((t-butyldimethylsilyl)oxy)- 1-phenyl-2-carboxylic acid and 0.095 ml (0.68 mmol) of triethylamine in 5 ml of dimethylformamide was treated sequentially with 92 mg (0.68 mmol) of 1-hydroxybenzotriazole and 130 mg (0.68 mmol) of ethyl (dimethylaminopropyl)carbodiimide hydrochloride. The resulting mixture was stirred for 15 min, then treated with 51 mg (0.34 mmol) of (1S,2R)-1-aminoindan-2-ol (J. Med. Chem., 1992, 35, 1685–1701) and stirred at ambient temperature for 16 h. The resulting solution was partitioned between ethyl acetate and water. The organic layer was washed with 1 N HCl, saturated aqueous NaHCO$_3$, water, and saturated brine. After being dried over MgSO$_4$, the organic phase was concentrated in vacuo. Silica gel chromatography of the residue using first 2% methanol in chloroform provided 215 mg (82%) of the desired compound (R$_f$ 0.5, 10% methanol in chloroform). $^1$H NMR (CDCl$_3$)δ0.01 (s, 3H), 0.05 (s, 3H), 0.87 (s, 9H), 1.34 (s, 9H), 2.15 (m, 1H), 2.29 (dd, J=12, 4 Hz, 1H), 2.50 (m, 2H), 2.69 (dd, J=9, 4 Hz, 1H), 2.8–2.9 (m, 4H), 3.0–3.1 (m, 5 H), 3.88 (m, 1H), 3.97 (m, 1H), 4.1–4.25 (m, 2H), 5.13 (AA', 2H), 5.26 (dd, J=8, 5 Hz, 1H), 5.67 (br, 1H), 6.50 (br, 1H), 7.1–7.4 (m, 14H). Mass spectrum: (M+H)$^+$=771.

K. (1S,2R,2'R,4'S,2"S)-1-((2-Benzy-5-((( 4-(benzyloxycarbonyl) -2-(t-butyl)amino)carbonyl)piperazin-1-yl) -4-hydroxypentanoyl)amino)indan-2-ol (1S,2R,2'R,4'S,2"S)-1-((2-benzyl-5-(((4-(benzyloxycarbonyl)- 2-(t-butyl)amino)carbonyl)piperazin-1-yl)-4-((t-butyldimethylsilyl)oxy)pentanoyl)amino)indan- 2-ol (215 mg (0.28 mmol) was treated with 2.8 ml (2.8 mmol) of 1 M tetra-n-butylammonium fluoride in tetrahydrofuran. The resulting solution was stirred at ambient temperature for 16 h, concentrated in vacuo, and diluted with ethyl acetate. The resulting solution was washed sequentially with two portions of water and one portion of saturated brine. The combined aqeous layers were extracted with ethyl acetate, and the combined organic layers were dried liver MgSO$_4$ and concentrated in vacuo. Silica gel chromatography of the residue using first 1% then 2% methanol in chloroform provided 95 mg (52%) of the desired compound as a solid. $^1$H NMR (d$_6$-DMSO)δ1.21 (s, 9H), 1.91 (m, 1H), 2.17 (m, 2H), 2.33 (m, 1H), 2.6 (m, 2H), 2.71 (m, 1H), 2.79 (br d, J=15 Hz, 1H), 2.9–3.2 (m, 6H), 3.67 (m, 4H), 4.31 (m, 1H), 4.68 (d, J=5 Hz, 1H), 4.85 (d, J=4 Hz, 1H), 5.08 (s, 2H), 5.16 (dd, J=9, 5 Hz, 1H), 7.1–7.4 (m, 14H), 7.75 (d, J=8 Hz, 1H). Mass spectrum: (M+ H)$^+$=657.

L. (1S,2R,2'R,4'S,2"S)-1-((2-Benzyl-5-((( 2-(t-butyl)amino)carbonyl)piperazin-1- yl)-4-hydroxypentanoyl)amino)indan-2-ol A mixture of 880 mg (1.34 mmol) of (1S,2R,2'R,4'S,2"S)-1-((2-benzyl- 5-(((4-(benzyloxycarbonyl)-2-(t-butyl)amino)carbonyl)piperazin- 1-yl)-4-hydroxypentanoyl)amino)indan-2-ol and 350 mg of 10% palladium on carbon in 120 ml of methanol was stirred under H$_2$ atmosphere at ambient pressure for 16 h. The resulting mixture was treated with Celite and purged with a stream of N$_2$ gas to remove the solvent. The residue was diluted with chloroform, filtered through a pad of Celite, and concentrated in vacuo to provide 59 mg (89%) of the desired compound. Mass spectrum: (M+H)$^+$=523.

M. Thioformamide

To a cooled (0° C.) 2 L three neck round bottom flask equipped with an overhead stirrer charged with a solution of formamide (30.5 mL, 0.76 mol) in 1 L of diethyl ether was added 89 g (0.19 mol) of phosphorous pentasulfide in small portions. The reaction mixture was allowed to warm to ambient temperature, stirred for 2 h, filtered, and concentrated in vacuo to afford thioformamide as a yellow offensive smelling oil which was used without purification.

N. Ethyl 2-Chloro-2-formylacetate

To a three neck 2 L round bottom flask charged with potassium t-butoxide (0.5 mol, 500 mL of a 1 M solution in THF) and 500 mL of dry THF cooled to 0° C. was added dropwise from an addition funnel a solution of ethyl chloroacetate (0.5 mol, 53.5 mL) and ethyl formate (0.5 mol, 40.4 mL), in 200 mL of THF over 3 hours. After completion of addition, the reaction mixture was stirred for 1 hour and allowed to stand overnight. The resulting solid was diluted with diethyl ether and cooled in an ice bath. Then, the pH was lowered to approximately 3 using 6N HCl. The organic phase was separated, and the aqueous layer was washed 3 times with diethyl ether. The combined ethereal portions were dried over NaSO$_4$, and concentrated in vacuo. The crude desired compound was stored at −30° C. and used without further purification.

O. Ethyl Thiazole-5-carboxylate

To a round bottom flask was added 250 mL of dry acetone, 7.5 g (0.123 mol) of thioformamide, and 18.54 g (0.123 mol) of ethyl 2-chloro- 2-formylacetate. The reaction was heated at reflux for 2 hours. The solvent was removed in vacuo, and the residue was purified by chromatography (SiO$_2$, 6 cm o.d. column, 100% CHCl$_3$, R$_f$=0.25) to provide 11.6 g (60%) of the desired compound as a light yellow oil. NMR (CDCl$_3$)δ1.39 (t, J=7 Hz, 3H), 4.38 (q, J=7 Hz, 2H), 8.50 (s, 1 H), 8.95 (s, 1H).

P. 5-(Hydroxymethyl)thiazole

To a precooled (ice bath) three neck 500 mL flask containing lithium aluminum hydride (76 mmol) in 250 mL of THF was added ethyl thiazole-5-carboxylate (11.82 g, 75.68 mmol) in 100 mL of THF dropwise over 1.5 hours to avoid excess foaming. The reaction was stirred for an additional hour, and treated cautiously with 2.9 mL of water, 2.9 mL of 15% NaOH, and 8.7 mL of water. The solid salts were filtered, and the flitrate set aside. The crude salts were heated at reflux in 100 mL of ethyl acetate for 30 min. The resulting mixture was filtered, and the two filtrates were combined, dried over Na$_2$SO$_4$, and concentrated in vacuo. The product was purified by silica gel chromatography eluting sequentially with 0% –2%–4% methanol in chloroform, to provide the desired compound, Rf=0.3 (4% methanol in chloroform), which solidified upon standing in 75% yield. NMR (CDCl$_3$)δ4.92 (s, 2H), 7.78 (s, 1H), 8.77 (s, 1H). Mass spectrum: (M+ H)$^+$=116.

Q. 5-(Chloromethyl)thiazole

A mixture of 1.0 g (8.69 mmol) of 5-(hydroxymethyl)thiazole, 1.82 ml (10.4 mmol) of diisopropylethylamine, and 7.3 g (174 mmol) of lithium chloride in 85 ml of chloroform was cooled to −50° C. and treated dropwise with 0.74 ml (9.56 mmol) of methanesulfonyl chloride. The resulting mixture was stirred at −50° C. for 1 h and 0° C. for 1 h, after which 100 ml of tetrahydrofuran was added and stirring was continued. After 0.5 h, the solvent was removed in vacuo, and the residue was purified by silica gel chromatography using 20% ethyl acetate in chloroform to provide 796 mg (68%) of the desired compound. $^1$H NMR (CDCl$_3$)δ4.85 (s, 2H), 7.86 (s, 1H), 8.82 (s, 1H). Mass spectrum: (M+H)$^+$= 134.

R. (1S,2R,2'R,4'S,2"S)-1-((2-Benzyl-5-(((2-(t-butyl) amino)carbonyl)- 4-((thiazol-5-yl)methyl)piperazin-1-yl)-4- hydroxypentanoyl)amino)indan- 2-ol A solution of 133 mg (0.25 mmol) of (1S,2R,2'R,4'S,2"S)-1-((2-benzyl- 5-(((2-(t-butyl)amino)carbonyl)piperazin-1-yl)-4-hydroxypentanoyl)amino)indan- 2-ol and 0.052 ml (0.3 mmol) of diisopropylethylamine in 1 ml of dimethylformamide was treated with 35 mg (0.25 mmol) of 5-(chloromethyl)thiazole. After being stirred at ambient temperature for 1 h, the mixture was treated with an additional portion of diisopropylethylamine (0.052 ml) and 5-(chloromethyl)thiazole (35 mg). After being stirred for an additional 40 min, a third portion of diisopropylethylamine (0.052 ml) and 5-(chloromethyl)thiazole (35 mg) was added. The resulting solution was stirred for 16 h, treated with a fourth portion of diisopropylethylamine (0.052 ml) and 5-(chloromethyl)thiazole (35 mg), and stirred for 4 h. The solution was subsequently diluted with 350 ml of ethyl acetate, washed with three 75 ml portions of water followed by 75 ml of saturated brine. The organic phase was dried over MgSO$_4$ and concentrated in vacuo. Silica gel chromatography of the residue using first 2%, then 6%, then 10% methanol in chloroform provided 141 mg (89%) of the desired compound, which was triturated with dichloromethane/hexane to give a white solid. $^1$H NMR (CDCl$_3$)δ1.39 (s, 9H), 1.96 (m, 1H), 2.32 (m, 1H), 2.5–3.1 (br envelope)3.19 (m, 1H), 3.7–3.85 (m, 4H), 4.27 (m, 1H), 5.28 (dd, J=8, 5 Hz, 1H), 5.92 (br d, J= 9 Hz, 1H), 7.1–7.35 (m, 14H), 7.69 (br, 1H), 7.73 (s, 1H), 8.80 (s, 1 H). Mass spectrum: (M+H)$^+$=620.

EXAMPLE 2

A. 2-Methylpropane-thioamide

A suspension of 100 g (1.15 mol) of isobutyramide in 4 L of diethyl ether was stirred vigorously and treated in portions with 51 g (0.115 mol) of P$_4$S$_{10}$. The resulting mixture was stirred at ambient temperature for 2 h, filtered, and concentrated in vacuo to provide 94.2 g (80%) of the crude desired compound. $^1$H NMR (DMSO-d$_6$)δ1.08 (d, J=7 Hz, 6H), 2.78 (heptet, J=7 Hz, 1H), 9.06 (br, 1H), 9.30 (br, 1 H). Mass spectrum: (M+H)$^+$=104.

B. 4-(Chloromethyl)-2-isopropylthiazole Hydrochloride

A mixture of 94.0 g (0.91 mol) of 2-methylpropane-thioamide, 115.7 g (0.91 mol) of 1,3-dichloroacetone, and 109.7 g (0.91 mol) of MgSO$_4$ in 1.6 liters of acetone was heated at reflux for 3.5 h. The resulting mixture was allowed to cool, filtered, and the solvent was removed in vacuo to provide the crude desired compound as a yellow oil. $^1$H NMR (DMSO-d$_6$) d 1.32 (d, J=7 Hz, 6H), 3.27 (heptet, J=7 Hz, 1H), 4.78 (s, 2H), 7.61 (s, 1H). Mass spectrum: (M+H)$^+$ =176.

C. (1S,2R,2'R,4'S,2"S)-1-((2-Benzyl-5-(((2-(t-butyl) amino)carbonyl)- 4-((2-isopropylthiazol-4-yl)methyl)piperazin-1-yl)-4- hydroxypentanoyl)amino)indan-2-ol Using the procedure of Example 1R, but replacing 5-(chloromethyl)thiazole with 4-chloromethyl-2-isopropylthiazole and doubling the proportion of diisopropylethylamine provided the desired compound.

EXAMPLE 3

A. Methyl 4-isopropyl-2-thiazolecarboxylate

A mixture of 2.11 g (12.8 mmol) of 1-bromo-3-methylbutan-2-one (Gaudry and Marquet, Tetrahedron, 26, 5661 (1970)), 1.0 g (12.8 mmol) of ethyl thiooxamate, and 1.70 g (14 mmol) of MgSO$_4$ in 50 ml of acetone was heated at reflux for 3 h. After being allowed to cool, the mixture was filtered, concentrated in vacuo, and purified by silica gel chromatography using chloroform to provide 0.29 g (11%) of the desired compound (R$_f$ 0.9, 4% methanol in chloroform). $^1$H NMR (DMSO-d$_6$)δ1.27 (d, J=7 Hz, 6H), 1.32 (t, J=7 Hz, 3H), 3.12 (heptet, J=7 Hz, 1H), 4.37 (q, J=7 Hz, 2H), 7.73 (s, 1H). Mass spectrum: (M+ H)$^+$=200.

B. 2-(Hydroxymethyl)-4-isopropylthiazole

Using the procedure of Example 1P, but replacing ethyl thiazole- 5-carboxylate with methyl 4-isopropyl-2-thiazolecarboxylate provided, after silica gel chromatography using 2% methanol in chloroform, the desired compound (R$_f$ 0.3, 5% methanol in chloroform) in 96% yield.

C. 2-(Chloromethyl)4-isopropylthiazole

Using the procedure of Example 1Q, but replacing 5-(hydroxymethyl)thiazole with 2-(hydroxymethyl)-4-isopropylthiazole provided the desired compound.

D. (1S,2R,2'R,4'S,2"S)-1-((2-Benzyl-5-(((2-(t-butyl) amino)carbonyl)- 4-((4-isopropylthiazol-2-yl)methyl)piperazin-1-yl)-4- hydroxypentanoyl)amino)indan-2-ol Using the procedure of Example 1R, but replacing 5-(chloromethyl)thiazole with 2-(chloromethyl)4-isopropylthiazole provided the desired compound.

EXAMPLE 4

A. Methyl Isocyanide

A 100 mL 3-neck flask (equipped with septum, stopper, and a short path mini distillation head with cow collector cooled to −78° C.) was charged with p-toluenesulfonyl chloride (36.25 g, 0.1901 mol) and quinoline (60 mL). The vigorously stirred solution was heated to 75° C. with the system under vacuum (H$_2$O aspirator with trap cooled to −40° C.). Neat N-methylformamide (7.50 g, 0.127 mol) was added via syringe in small portions over 15 mins. The increasingly viscous solution was heated for 10 mins, at which time gas evolution had ceased. Material in the cow collector and in the vacuum trap were combined and vacuum distilled to provide the compound as a colorless liquid (2.06 g, 0.0502 mol, 39%).

B. 5-((Diethoxy)methyl)oxazole

Prepared according to the procedure of Schöllkopf (J. Am. Chem. Soc. 112 (10) 4070 (1990)). To a solution of methyl isocyanide (2.88 g, 0.0702 mol) in THF (50 mL) under argon at −78° C. was added dropwise n-butyllithium solution (1.6M in hexanes, 44 mL) over 15 mins. After stirring for an additional 20 mins at −78° C., a solution of ethyl diethoxyacetate (12.62 g, 0.0702 mol) in THF (15 mL) was added dropwise over 20 mins. The bath was allowed to warm to −30° C. over the next 2 hrs and the reaction was then stirred at 0° C. for 30 mins. The reaction was quenched at 0° C. with glacial HOAc (4.22 g, 0.0702 mol) and the solvent was removed by rotary evaporation in vacuo. The golden solid was partitioned with H$_2$O (45 mL) and EtOAc (200 mL), and the aqueous extracted with EtOAc (2×200 mL). The combined organic was washed with satd aq NaCl, dried over Na$_2$SO$_4$, and concentrated in vacuo to a brown oil. Chromatography on a 300 g SiO$_2$ flash column with a gradient of EtOAc/hexane (10%, 15%, 20%) afforded the desired compound as a colorless liquid (7.46 g, 0.0436 mol, 62%): $^1$H NMR (CDCl$_3$)δ1.25 (t, J=6.9 Hz, 6H), 3.56–3.70 (m, 4H), 5.62 (s, 1H), 7.26 (s, 1H), 7.86 (s, 1H). Mass spectrum: (M+H)$^+$= 172.

C. 5-Oxazolecarboxaldehyde

A flask was charged with 5-((diethoxy)methyl)oxazole (1.02 g, 0.00596 mol) and cooled to 0° C. A solution of trifluoroacetic acid/$CH_2Cl_2$ (1:1 (v/v), 6.7 mL) and $H_2O$ (0.39 mL) was added and the solution stirred at 0° C. for 10 min. The solvent was removed in vacuo, and the residue was treated with toluene and concentrated. Chromatography on a 100 g $SiO_2$ flash column with a gradient of EtOAc/hexane (20%, 30%, 40%) afforded the desired compound as a colorless liquid (0.344 g, 0.00354 mol, 59%): $^1$H NMR ($CDCl_3$) d 7.89 (s, 1H), 8.12 (s, 1H), 9.87 (s, 1H). Mass spectrum: $(M+H)^+=98$.

D. 5-(Hydroxymethyl)oxazole

A solution of 5-oxazolecarboxaldehyde (0.627 g, 0.00646 mol) in MeOH (10 mL) under argon at 0° C. was treated with $NaBH_4$ (0.247 g, 0.00646 mol). After 5 mins the reaction was quenched with acetone and the solvent removed by rotary evaporation in vacuo. Chromatography on a 100 g $SiO_2$ flash column with a gradient of MeOH/$CH_2Cl_2$ (5%, 10%) afforded the desired compound as a colorless oil (0.408 g, 0.00412 mol, 64%): $^1$H NMR ($CDCl_3$)$\delta$2.03 (t, J=6.0 Hz, 1H), 4.70 (d, J=6.0 Hz, 2H), 7.04 (s, 1H), 7.87 (s, 1H). MS (Cl/$NH_3$) m/e 117 (m+$NH_4$), 100 (m+H).

E. 5-(Chloromethyl)oxazole

Using the procedure of Example 1Q, but replacing 5-(hydroxymethyl)thiazole with 5-(hydroxymethyl)oxazole provided the desired compound.

F. (1S,2R,2'R,4'S,2"S)-1-((2-Benzyl-5-(((2-(t-butyl)amino)carbonyl)-4((oxazol-5-yl)methyl)piperazin-1-yl)-4-hydroxypentanoyl)amino)indan- 2-ol Using the procedure of Example 1R, but replacing 5-(hydroxymethyl)thiazole with 5-(chloromethyl)oxazole provided the desired compound.

EXAMPLE 5

A. 4-Chloromethyl-4-hydroxy-2-isopropyloxazoline

To a solution of isobutyramide (9.876 g, 0.1122 mol) in acetone (130 mL) was added 1,3-dichloroacetone (10.0 g, 0.0748 mol), $NaHCO_3$ (9.429 g, 0.1122 mol), and $MgSO_4$ (18.01 g, 0.1496 mol). The mixture was heated at reflux under argon for 63 hrs, then cooled to room temperature, vacuum filtered, and concentrated in vacuo to a dark brown semi-solid. The residue was purified by $SiO_2$ flash chromatography using a gradient of EtOAc/$CH_2Cl_2$ (5%, 10%, 20%, 40%) to obtain the desired product as an orange liquid (6.06 g, 0.0341 mol, 46%): $^1$H NMR ($CDCl_3$)$\delta$1.20–1.28 (m, 6H), 2.56–2.72 (m, 1H), 3.70 (s, 2H), 4.18 (d, J=9.6 Hz, 1H), 4.38 (d, J=9.6 Hz, 1H). Mass spectrum: $(M+H)^+=178, 180$.

B. 4-Chloromethyl-2-isopropyloxazole

A solution of 4-chloromethyl-4-hydorxy-2-isopropyloxazoline (4.88 g, 0.0275 mol) in 1,2-dichloroethane (20 mL) was added to a solution of $SOCl_2$ (2.40 mL, 0.0329 mol) in 1,2-dichloroethane (80 mL) at 0° C. under argon, and the solution was heated to 70° C. After 15 min at 70° C., the reaction was cooled to room temperature and the solvent removed by rotary evaporation in vacuo. Drying the residue on high vacuum gave the desired compound as a brown semi-solid (4.20 g, 0.0263 mol, 96%): $^1$H NMR ($CDCl_3$)$\delta$1.36 (d, J=7.5 Hz, 6H), 3.03–3.18 (m, 1H), 4.50 (s, 2H), 7.56 (s, 1H). Mass spectrum: $(M+H)^+=160, 162$.

C. (1S,2R,2'R,4'S,2"S)-1-((2-Benzyl-5-(((2-(t-butyl)amino)carbonyl)-4-((2-isopropyloxazol-4-yl)methyl)piperazin-1-yl)-4-hydroxypentanoyl)amino)indan-2-ol Using the procedure of Example 1R, but replacing 5-(chloromethyl)thiazole with 4-chloromethyl-2-isopropyloxazole provided the desired compound.

ESAMPLE 6

A. 4-(Chloromethyl)thiazole

Using the procedure of Example 2B but replacing 2-methylpropane-thioamide with thioformamide provided the crude desired compound.

B. (1S,2R,2'R,4'S,2"S)-1-((2-Benzyl-5-(((2-(t-butyl)amino)carbonyl)-4-((thiazol-4-yl)methyl)piperazin-1-yl)-4-hydroxypentanoyl)amino)indan-2-ol Using the procedure of Example 1R, but replacing 5-(chloromethyl)thiazole with 4-(chloromethyl)thiazole and doubling the proportion of diisopropylethylamine provided the desired compound.

EXAMPLE 7

A. Ethyl 2-Methylthiazole-5-carboxylate

Using the procedure of Example 1O but replacing thioformamide with thioacetamide provided the crude desired compound.

B. 5-(Hydroxymethyl)-2-methylthiazole

Using the procedure of Example 1P, but replacing ethyl thiazole- 5-carboxylate with crude ethyl 2-methylthiazole-5-carboxylate provided, after silica gel chromatography using 3% then 5% methanol in chloroform, the desired compound, $R_f$ 0.27, (4% methanol in chloroform) in 78% yield. $^1$H NMR ($CDCl_3$)$\delta$2.32 (br, 1H), 2.70 (s, 3 H), 4.80 (s, 2H), 7.46 (s, 1H). Mass spectrum: $(M+H)^+=130$.

C. 2-(Chloromethyl)-2-methylthiazole

Using the procedure of Example 1Q, but replacing 5-(hydroxymethyl)thiazole with 5-(hydroxymethyl)-2-methylthiazole provided the desired compound.

D. (1S,2R,2'R,4'S,2"S)-1-((2-Benzyl-5-(((2-(t-butyl)amino)carbonyl)-4-((2-methylthiazol-5-yl)methyl)piperazin-1-yl)-4-hydroxypentanoyl)amino)indan-2-ol Using the procedure of Example 1R, but replacing 5-(chloromethyl)thiazole with 2-(chloromethyl)-2-methylthiazole provided the desired compound.

EXAMPLE 8

A. 4-(Chloromethyl)-2-(dimethylamino)thiazole

A mixture of 15 g (144 mmol) of N,N-dimethylthiourea and excess $MgSO_4$ in 350 ml of acetone was heated to reflux and treated dropwise with a solution of 18.3 g (144 mmol) of 1,3-dichloroacetone in 35 ml of acetone. The resulting mixture was heated at reflux for 1.5 h, allowed to cool, filtered, and concentrated in vacuo. The residue was purified by silica gel chromatography using 20% ethyl acetate in hexane to provide 14.0 g (70%) of the desired compound.

B. (1S,2R,2'R,4'S,2"S)-1-((2-Benzyl-5-(((2-(t-butyl)amino)carbonyl)-4-((2-(dimethylamino)thiazol-4-yl)methyl)piperazin-1-yl)- 4-hydroxypentanoyl)amino ) indan-2-ol Using the procedure of Example 1R, but replacing 5-(chloromethyl)thiazole with 4-(chloromethyl)-2-(dimethylamino)thiazole provided the desired compound.

EXAMPLE 9

A. 4-((Amino)thiocarbonyl)morpholine

A solution of 3.35 g (18.8 mmol) of thiocarbonyl diimidazole in 100 ml of THF was treated with 0.82 ml (9.4 mmol) of morpholine. After being stirred at ambient temperature for 3.5 h, an additional 0.82 ml portion of morpholine was added, and stirring was continued. After 6 h, the solution was treated with excess concentrated aqueous ammonia, and stirred overnight. The resulting solution was concentrated in vacuo, taken up in chloroform, separated from the aqueous phase, dried over $Na_2SO_4$, and concentrated. Purification of the residue by silica gel chromatography using ethyl acetate provided 1.85 g (76%) of the desired compound, $R_f$ 0.17 (10% methanol in chloroform), as a white solid. $^1H$ NMR $(CDCl_3)$ δ3.76 (m, 4H), 3.83 (m, 4H), 5.75 (br, 2 H). Mass spectrum: $(M+H)^+$=147.

B. Ethyl 2-(4-Morpholinyl)thiazole-4-carboxylate

A mixture of 1.85 g (12.7 mmol) of 4-((amino)thiocarbonyl)morpholine, 1.59 ml (12.7 mmol) of ethyl bromopyruvate, and excess $MgSO_4$ in 50 ml of acetone was heated at reflux for 2 h. The resulting mixture was allowed to cool, filtered, and concentrated in vacuo. The residue was taken up in chloroform, washed with aqueous $NaHCO_3$, dried over $Na_2SO_4$, and concentrated. Silica gel chromatography using 1% methanol in chloroform provided 1.7 g (55%) of the desired compound, $R_f$ 0.70 (ethyl acetate). Mass spectrum: $(M+H)^+$=243.

C. 2-(4-Morpholinyl)-4-(hydroxymethyl)thiazole

A solution of 7.0 ml (7.0 mmol) of lithium aluminum hydride in toluene was diluted with 10 ml of THF, cooled to 0° C., and treated with a solution of 1.7 g (7.0 mmol) of ethyl 2-(4-morpholinyl)thiazole-4-carboxylate in 25 ml of THF. The resulting solution was stirred for 1 h, quenched cautiously with aqueous Rochelle's salts, diluted with chloroform, filtered, dired over $Na_2SO_4$, and concentrated in vacuo. Silica gel chromatography using 2–4% methanol in chloroform provided 856 mg (61%) of the desired compound, $R_f$ 0.16 (4% methanol in chloroform). $^1H$ NMR $(CDCl_3)$δ2.44 (br, 1H), 3.46 (t, J=5 Hz, 4H), 3.81 (t, J=5 Hz, 1H), 4.55 (br s, 2H), 6.45 (s, 1H). Mass spectrum: $(M+H)^+$=200.

D. 4-(Chloromethyl)-2-(4-morpholinyl)thiazole

Using the procedure of Example 8A but replacing N,N-dimethylthiourea with 2-(4-morpholinyl)-4-(hydroxymethyl)thiazole provided the desired compound.

E. (1S,2R,2'R,4'S,2"S)-1-((2-Benzyl-5-(((2-(t-butyl)amino)carbonyl)-4-((2-(4-morpholinyl)thiazol-4-yl)methyl)piperazin-1-yl)-4-hydroxypentanoyl)amino)indan-2-ol Using the procedure of Example 1R, but replacing 5-(chloromethyl)thiazole with 4-(chloromethyl)-2-(4-morpholinyl)thiazole provided the desired compound.

EXAMPLE 10

A. 1-((Amino)thiocarbonyl)pyrrolidine

Using the procedure of Example 9A but replacing morpholine with pyrrolidine, and stirring the solution for six days after addition of aqueous ammonia provided the desired compound. $^1H$ NMR $(CDCl_3)$δ 1.97 (m, 2H), 2.11 (m, 2H), 3.38 (br t, 2H), 3.85 (br t, 2H), 5.56 (br, 2 H). Mass spectrum: $(M+H)^+$=131.

B. Ethyl 2-(1-Pyrrolidinyl)thiazole-4-carboxylate

Using the procedure of Example 9B but replacing 4-((amino)thiocarbonyl)morpholine with 1-((amino)thiocarbonyl)pyrrolidine provided the desired compound. $^1H$ NMR $(CDCl_3)$δ1.37 (t, J=7 Hz, 3H), 2.04 (m, 4H), 3.51 (m, 4H), 4.35 (q, J=7 Hz, 2H), 7.37 (s, 1H). Mass spectrum: $(M+H)^+$=227.

C. 2-(1-Pyrrolidinyl)-4-(hydroxymethyl)thiazole

Using the procedure of Example 9C but replacing ethyl 2-(4-morpholinyl)thiazole- 4-carboxylate with ethyl 2-(1-pyrrolidinyl)thiazole- 4-carboxylate provided, after silica gel chromatography using 2–4% methanol in chloroform, the desired compound ($R_f$ 0.26, 4% methanol in chloroform)in 53% yield. $^1H$ NMR $(CDCl_3)$δ2.04 (m, 4H), 2.75 (br, 1H), 3.45 (m, 4H), 4.56 (s, 2H), 6.32 (s, 1H). Mass spectrum: $(M+ H)^+$=185.

D. 4-(Chloromethyl)-2-(1-pyrrolidinyl)thiazole

Using the procedure of Example 8A but replacing N,N-dimethylthiourea with 2-(1-pyrrolidinyl)-4-(hydroxymethyl)thiazole provided the desired compound.

E. (1S,2R,2'R,4'S,2"S)-1-((2-Benzyl-5-(((2-(t-butyl)amino)carbonyl)-4-((2-(1-pyrrolidinyl)thiazol-4-yl)methyl)piperazin-1-yl)- 4-hydroxypentanoyl)amino)indan-2-ol Using the procedure of Example 1R, but replacing 5-(chloromethyl)thiazole with 4-(chloromethyl)-2-(1-pyrrolidinyl)thiazole provided the desired compound.

EXAMPLE 11

A. 2-Methoxythioacetamide

Using the procedure of Example 2A but replacing isobutyramide with 2-methoxyacetamide provided the desired compound in 52% yield.

B. 4-(Chloromethyl)-2-(methoxymethyl)thiazole hydrochloride

Using the procedure of Example 2B but replacing 2-methylpropane-thioamide with 2-methoxythioacetamide provided the crude desired compound in 41% yield.

C. (1S,2R,2'R,4'S,2"S)-1-((2-Benzyl-5-(((2-(t-butyl)amino)carbonyl)- 4((2-(methoxymethyl)thiazol-4-yl)methy)piperazin-1-yl)-4-hydroxypentanoyl)amino)indan-2-ol Using the procedure of Example 1R, but replacing 5-(chloromethyl)thiazole with 4-(chloromethyl)-2-(methoxymethyl)thiazole hydrochloride and doubling the proportion of diisopropylethylamine provided the desired compound.

EXAMPLE 12

A. Cyclopentanethiocarboxamide

Using the procedure of Example 2A, but replacing isobutyramide with cyclopentanecarboxamide provided 2.4 g (83%) of the crude desired compound.

B. 4-(Chloromethyl)-2-cyclopentylthiazole hydrochloride

Using the procedure of Example 2B, but replacing 2-methylpropane-thioamide with cyclopentanethiocarboxamide provided the crude desired compound as a yellow oil. C. (1S,2R,2'R,4'S,2"S)-1-((2-Benzyl-5-(((2-(t-butyl)amino)carbonyl)- 4-((2-cyclopentylthiazol-4-yl)methyl)piperazin-1-yl)- 4-hydroxypentanoyl)amino)indan-2-ol Using the procedure of Example 1R, but replacing 5-(chloromethyl)thiazole with 4-(chloromethyl)-2-cyclopentylthiazole hydrochloride and doubling the proportion of diisopropylethylamine provided the desired compound.

Fluorogenic Assay for Screening Inhibitors of HIV Protease

The inhibitory potency of the compounds of the invention can be determined by the following method.

A compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1 M sodium chloride, 5 mM dithiothreitol, 0.5 mg/ml bovine serum albumin, 1.3 μM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmision 490 nM) is recorded as a function of time. The reaction rate is determined for the first six to eight minutes. The observed rate is directly proportional to the moles of substrate cleaved per unit time. The percent inhibition is 100 X (1 -(rate in presence of inhibitor)/(rate in absence of inhibitor)).

Fluorogenic substrate: Dabcyl-Ser-Gln-Asn-Tyr-Pro-Ile-Val-Gln-EDANS wherein DABCYL=4-(4-dimethylaminophenyl)azobenzoic acid and EDANS=5-((2-aminoethyl)amino)-naphthalene-1-sulfonic acid.

Table 1 shows the inhibitory potencies of compounds of the invention against HIV-1 protease.

TABLE 1

| Compound of Example | Percent Inhibition | Inhibitor Concentration (nanomolar) |
|---|---|---|
| 1R | 61 | 0.5 |

Antiviral Activity

The anti-HIV activity of the compounds of the invention can be determined in MT4 cells according to the procedure of Kempf, et. al. (Antimicrob. Agents Chemother. 1991, 35, 2209). The $IC_{50}$ is the concentration of compound that gives 50% inhibition of the cytopathic effect of HIV. The $LC_{50}$ is the concentration of compound at which 50% of the cells remain viable.

Table 2 shows the inhibitory potencies of compounds of the invention against HIV-$1_{3B}$ in MT4 cells.

TABLE 2

| Compound of Example | $IC_{50}$ (micromolar) | $LC_{50}$ (micromolar) |
|---|---|---|
| 1R | 0.016 | >100 |

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

Preferred salts of the compounds of the invention include hydrochloride, methanesulfonate, sulfonate, phosphonate and isethionate.

The compounds of the present invention can also be used in the form of esters. Examples of such esters include a hydroxyl-substituted compound of formula A1 or A2 or A3 or A4 which has been acylated with a blocked or unblocked amino acid residue, a phosphate function, a hemisuccinate residue, an acyl residue of the formula R*C(O)— or R*C(S)— wherein R* is hydrogen, loweralkyl, haloalkyl, alkoxy, thioalkoxy, alkoxyalkyl, thioalkoxyalkyl or haloalkoxy, or an acyl residue of the formula $R_a$—C($R_b$)($R_d$)— C(O)— or $R_a$—C(Rb)($R_d$)—C(S)— wherein $R_b$ and $R_d$ are independently selected from hydrogen or loweralkyl and $R_a$ is —N($R_e$)($R_f$), O$R_e$ or —S$R_e$ wherein $R_e$ and $R_f$ are independently selected from hydrogen, loweralkyl and haloalkyl, or an amino-acyl residue of the formula $R_{180}$NH(CH$_2$)$_2$NHCH$_2$C(O)— or $R_{180}$NH(CH$_2$)$_2$OCH$_2$C(O)— wherein $R_{180}$ is hydrogen, loweralkyl, arylalkyl, cycloalkylalkyl, alkanoyl, benzoyl or an a-amino acyl group. The amino acid esters of particular interest are glycine and lysine; however, other amino acid residues can also be used, including those wherein the amino acyl group is —C(O)CH$_2$N$R_{200}$$R_{201}$ wherein $R_{200}$ and $R_{201}$ are independently selected from hydrogen and loweralkyl or the group —N$R_{200}$$R_{201}$ forms a nitrogen containing heterocyclic ring. These esters serve as pro-drugs of the compounds of the present invention and serve to increase the solubility of these substances in the gastrointestinal tract. These esters also serve to increase solubility for intravenous administration of the compounds. Other prodrugs include a hydroxyl-substituted compound of formula A1 or A2 or A3 or A4 wherein the hydroxyl group is functionalized with a substituent of the formula —CH($R_g$)OC(O)$R_{181}$ or —CH($R_g$)OC(S)$R_{181}$ wherein $R_{181}$ is loweralkyl, haloalkyl, alkoxy, thioalkoxy or haloalkoxy and $R_g$ is hydrogen, loweralkyl, haloalkyl, alkoxycarbonyl, aminocarbonyl, alkylaminocarbonyl or dialkylaminocarbonyl. Such prodrugs can be prepared according to the procedure of Schreiber (Tetrahedron Lett. 1983, 24, 2363) by ozonolysis of the corresponding methallyl ether in methanol followed by treatment with acetic anhydride.

The prodrugs of this invention are metabolized in vivo to provide the hydroxyl-substituted compound of formula A1 or A2 or A3 or A4. The preparation of the prodrug esters is carried out by reacting a hydroxyl-substituted compound of formula A1 or A2 or A3 or A4 with an activated amino acyl, phosphoryl, hemisuccinyl or acyl derivative as defined above. The resulting product is then deprotected to provide the desired pro-drug ester. Prodrugs of the invention can also be prepared by alkylation of the hydroxyl group with (haloalkyl)esters, transacetalization with bis(alkanoyl)acetals or condensation of the hydroxyl group with an activated aidehyde followed by acylation of the intermediate hemiacetal.

The compounds of the invention are useful for inhibiting retroviral protease, in particular HIV protease, in vitro or in vivo (especially in mammals and in particular in humans). The compounds of the present invention are also useful for the inhibition of retroviruses in vivo, especially human immunodeficiency virus (HIV). The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors ( for example, dideoxycytidine (DDC), dideoxyinosine (DDI), BCH-189, AzdU, carbovir, DDA, D4C, D4T, DP-AZT, FLT (fluorothymidine), BCH-189, 5-halo-3'-thiadideoxycytidine, PMEA, zidovudine (AZT) and the like), non-nucleoside reverse transcriptase inhibitors (for example, R82193, L-697,661, BI-RG-587 (nevirapine), retroviral protease inhibitors (for example, HIV protease inhibitors such as Ro 31-8959, SC-52151, KNI-227, KNI-272 and the like), HEPT compounds, L,697,639, R82150, U-87201E and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclovir, castanospermine, rCD4/CD4-lgG, CD4-PE40, butyl-DNJ, hypericin, oxamyristic acid, dextran sulfate and pentosan polysulfate. Immunomodulators that can be administered in combination with a compound of the present invention include bropirimine, Ampligen, anti-human alpha interferon antibody, colony stimulting factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis facator, beta interferon, gamma interferon, interleukin-3, interleukin-4, autologous CDB+ infusion, alpha interferon immunoglobulin, IGF-1, anti-Leu-3A, autovaccination, biostimulation, extracorporeal photophoresis, FK-565, FK- 506, G-CSF, GM-CSF, hyperthermia, isopinosine, IVIG, HIVIG, passive immunotherapy and polio vaccine hyperimmunization. Other antiinfective agents that can be administered in combination with a compound of the present invention include pentamidine isethionate. Any of a variety of HIV or AIDS vaccines (for example, gp120 (recombinant), Env 2–3 (gp120), HIVAC-1e (gp120), gp160 (recombinant), VaxSyn HIV-1 (gp160), Immuno-Ag (gp160), HGP-30, HIV-Immunogen, p24 (recombinant), VaxSyn HIV-1 (p24) can be used in combination with a compound of the present invention.

Other agents that can be used in combination with the compounds of this invention are ansamycin LM 427, apurinic acid, ABPP, Al-721, carrisyn, AS-101, avarol, azimexon, colchicine, compound Q, CS-85, N-acetyl cysteine, (2-oxothiazolidine-4-carboxylate), D-penicillamine, diphenylhydantoin, EL-10, erythropoieten, fusidic acid, glucan, HPA-23, human growth hormone, hydroxchloroquine, iscador, Loofloxacin or other quinolone antibiotics, lentinan, lithium carbonate, MM-1, monolaurin, MTPPE, naltrexone, neurotropin, ozone, PAl, panax ginseng, pentofylline, pentoxifylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compounds of this invention are antifungals such as amphotericin B, clotrimazole, flucytosine, fluconazole, itraconazole, ketoconazole and nystatin and the like.

Other agents that can be used in combination with the compounds of this invention are antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like.

Other agents that can be used in combination with the compounds of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP(prednisone, methotrexate (w/leucovin rescue), doxorubicin, cyclophosphamide, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compounds of this invention are drugs for treating neurological disease such as peptide T, ritalin, lithium, elavil, phenytoin, carbamazipine, mexitetine, heparin and cytosine arabinoside and the like.

Other agents that can be used in combination with the compounds of this invention are anti-protozoals such as albendazole, azithromycin, clarithromycin, clindamycin, corticosteroids, dapsone, DIMP, eflornithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

Among the preferred agents for treatment of HIV or AIDS in combination with the compounds of this invention are reverse transcriptase inhibitors.

It will be understood that agents which can be combined with the compounds of the present invention for the treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

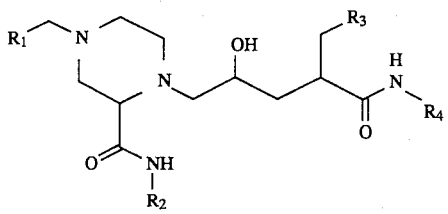

wherein R₁ is thiazolyl, oxazolyl, monosubstituted thiazolyl or monosubstituted oxazolyl wherein the substituent is selected from (i) loweralkyl, (ii) loweralkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy, (viii) (heterocyclic)alkyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, loweralkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

R₂ is loweralkyl;

R₃ is benzyl or benzyl in which the phenyl group is substituted with loweralkyl, —OH, halo, alkoxy, trifluoromethyl, 2-(4-morpholinyl)ethoxy or 2-hydroxyethoxy; and R₄ is

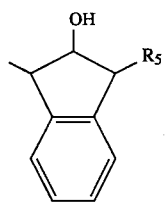

wherein R₅ is hydrogen, —OH or —NH₂; or a pharmaceutically acceptable salt, ester or prodrug thereof.

2. The compound of claim 1 wherein R₁ is thiazolyl, oxazolyl, monosubstitued thiazolyl or monosubstituted oxazolyl wherein the substituent is selected from loweralkyl, cycloalkyl or cycloalkylalkyl; R₂ is t-butyl, isopropyl or t-butylmethyl; R₃ is benzyl and R₅ is hydrogen.

3. A compound of the formula:

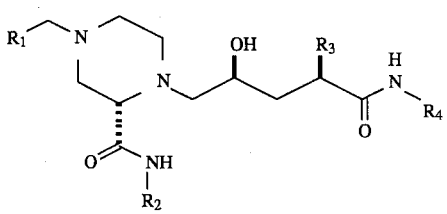

wherein R₁ is thiazolyl, oxazolyl, monosubstituted thiazolyl or monosubstituted oxazolyl wherein the substituent is selected from (i) loweralkyl, (ii) loweralkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy, (viii) (heterocyclic)alkyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, loweralkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

R₂ is loweralkyl;

R₃ is benzyl or benzyl in which the phenyl group is substituted with loweralkyl, —OH, halo, alkoxy, trifluoromethyl, 2-(4-morpholinyl)ethoxy or 2hydroxyethoxy; and R₄ is

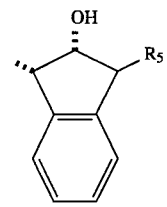

wherein R₅ is hydrogen, —OH or —NH₂; or a pharmaceutically acceptable salt, ester or prodrug thereof.

4. The compound of claim 3 wherein R₁ is thiazolyl, oxazolyl, monosubstitued thiazolyl or monosubstituted oxazolyl wherein the substituent is selected from loweralkyl, cycloalkyl or cycloalkylalkyl; R₂ is t-butyl, isopropyl or t-butylmethyl; R₃ is benzyl and R₄

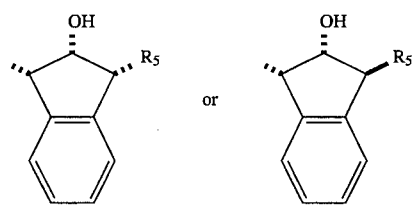

wherein R₅ is hydrogen, —OH or —NH₂.

5. The compound of claim 3 wherein R₁ is thiazolyl, oxazolyl, monosubstitued thiazolyl or monosubstituted oxazolyl wherein the substituent is selected from loweralkyl, cycloalkyl or cycloalkylalkyl; R₂ is t-butyl, isopropyl or t-butylmethyl; R₃ is benzyl and R₅ is hydrogen.

6. The compound (1S,2R,2'R,4'S,2"S)-1-((2-benzyl-5-(((2-(t-butyl)amino)carbonyl)-4-((thiazol-5-yl) methyl)piperazin-1-yl)- 4-hydroxypentanoyl)amino)indan-2-ol; or a pharmaceutically acceptable salt, ester or prodrug thereof.

7. A compound selected from the group consisting of:

(1S,2R,2'R,4'S,2"S)-1-((2-benzyl- 5-(((2-(t-butyl)amino)carbonyl)-4-((2-isopropylthiazol-4-yl)methyl)piperazin-1-yl)- 4-hydroxypentanoyl)amino)indan-2-ol;

(1S,2R,2'R,4'S,2"S)-1-((2-benzyl- 5-(((2-(t-butyl)amino)carbonyl)-4-((4-isopropylthiazol-2-yl)methyl)piperazin-1-yl)- 4-hydroxypentanoyl)amino)indan-2-ol;

(1S,2R,2'R,4'S,2"S)-1-((2-benzyl-5-(((2-(t-butyl)amino)carbonyl)-4-((oxazol-5-yl)methyl)piperazin-1-yl)-4-hydroxypentanoyl)amino)indan-2-ol:

(1S,2R,2'R,4'S,2"S)-1-((2-benzyl-5-(((2-(t-butyl)amino)carbonyl)-4-((2-isopropyloxazol-4-yl)methyl)piperazin-1-yl)-4-hydroxypentanoyl)amino)indan-2-ol;

(1S,2R,2'R,4'S,2"S)-1-((2-benzyl-5-(((2-(t-butyl)amino)carbonyl)-4-((thiazol-4-yl)methyl)piperazin-1-yl)-4-hydroxypentanoyl)amino)indan-2-ol;

(1S,2R,2'R,4'S,2"S)-1-((2-benzyl-5-(((2-(t-butyl)amino)carbonyl)-4-((2-methylthiazol-5-yl)methyl)piperazin-1-yl)-4-hydroxypentanoyl)amino)indan-2-ol;

1S,2R,2'R,4'S,2"S)-1-((2-benzyl-5-(((2-(t-butyl)amino)carbonyl)-4-((2-dimethylamino)thiazol-4-yl)methyl)piperazin-1-yl)-4-hydroxypentanoyl)amino)indan-2-ol;

(1S,2R,2'R,4'S,2"S)-1-((2-benzyl-5-(((2-(t-butyl)amino)carbonyl)-4-((2-4-morpholinyl)thiazol-4-yl)methyl)piperazin-1-yl)-4-hydroxypentanoyl)amino)indan-2-ol;

(1S,2R,2'R,4'S,2"S)-1-((2-benzyl-5-(((2-(t-butyl)amino)carbonyl)-4-((2-(1-pyrrolidinyl)thiazol-4-yl)methyl)piperazin-1-yl)-4-hydroxypentanoyl)amino)indan-2-ol;

(1S,2R,2'R,4'S,2"S)-1-((2-benzyl-5-(((2-(t-butyl)amino)carbonyl)-4-((2-methoxymethyl)thiazol-4-yl)methyl)piperazin-1-yl)-4-hydroxypentanoyl)amino)indan-2-ol; and (1S,2R,2'R,4'S,2"S)-1-((2-benzyl-5-(((2-(t-butyl)amino)carbonyl)-4-((2-cyclopentylthiazol-4-yl)methyl)piperazin-1-yl)-4-hydroxypentanoyl)amino)indan-2-ol;

or a pharmaceutically acceptable salt, ester or prodrug thereof.

* * * * *